(12) United States Patent
Molnar et al.

(10) Patent No.: US 9,823,219 B2
(45) Date of Patent: Nov. 21, 2017

(54) ELECTROCHEMICAL DETECTION SYSTEM WITH INTERNAL LIFE-TEST

(71) Applicant: Rosemount Analytical Inc., Calgary (CA)

(72) Inventors: Zoltan I. Molnar, Calgary (CA); Carmine Pacifico, Calgary (CA)

(73) Assignee: Rosemount Analytical, Inc, Calgary, AB (CA)

( * ) Notice: Subject to any disclaimer, the term of this patent is extended or adjusted under 35 U.S.C. 154(b) by 156 days.

(21) Appl. No.: 14/576,672

(22) Filed: Dec. 19, 2014

(65) Prior Publication Data

US 2015/0177185 A1    Jun. 25, 2015

Related U.S. Application Data

(60) Provisional application No. 61/919,587, filed on Dec. 20, 2013.

(51) Int. Cl.
*G01N 27/416*    (2006.01)

(52) U.S. Cl.
CPC .................... *G01N 27/4163* (2013.01)

(58) Field of Classification Search
CPC ............ G01N 27/4163; G01N 27/416; G01N 27/4065; G01N 27/3272; G01N 27/404; G01N 27/28; G01N 33/48785; B60L 3/0069; B60L 2250/16; G01R 31/2829
See application file for complete search history.

(56) References Cited

U.S. PATENT DOCUMENTS

| | | | |
|---|---|---|---|
| 5,733,436 A | 3/1998 | Demisch et al. | |
| 6,123,818 A | 9/2000 | Lindsay | |
| 6,251,243 B1 | 6/2001 | Lindsay | |
| 6,428,684 B1 | 8/2002 | Warburton | |
| 6,456,085 B1 * | 9/2002 | Dietl ..................... | B60L 3/0069 324/509 |
| 8,180,466 B2 | 5/2012 | Longsdorf et al. | |
| 2005/0155406 A1 | 7/2005 | Studer et al. | |
| 2012/0032683 A1 | 2/2012 | Greif et al. | |

OTHER PUBLICATIONS

International Preliminary Report on Patentability for International Application No. PCT/US2014/071404, date of mailing: Jun. 30, 2016; date of filing: Dec. 19, 2014, 8 pages.
First Office Action from Chinese Patent Application No. 201480004025.7, dated Jul. 5, 2016, 19 pages.
International Seach Report and Written Opinion for Inernational Application No. PCT7US2014/071404, date of mailing. Apr. 15, 2015; date of filing: Dec. 19, 2014. 12 pages.
Extended European Search Report of European Patent Application No. 14872183.0, dated Jul. 3, 2017, 7 pages.

* cited by examiner

*Primary Examiner* — Xiuyu Tai
(74) *Attorney, Agent, or Firm* — Christopher R. Christenson; Kelly, Holt & Christenson, PLLC

(57) ABSTRACT

A detection system includes an electrochemical sensor. Measurement circuitry is coupled to the electrochemical sensor and configured to measure an electrical characteristic of the electrochemical sensor. A controller is coupled to the measurement circuitry and is configured to provide an indication based on the measured electrical characteristic. The controller is further configured to generate an electrical disturbance to the electrochemical sensor and obtain a sensor recovery profile to provide a diagnostic indication relative to the electrochemical sensor.

12 Claims, 4 Drawing Sheets

ELECTROCHEMICAL DETECTION SYSTEM WITH INTERNAL LIFE-TEST

CROSS-REFERENCE TO RELATED APPLICATIONS

The present application is based on and claims the benefit of U.S. Provisional Patent Application Ser. No. 61/919,587, filed Dec. 20, 2013, the content of which is hereby incorporated by reference in its entirety.

BACKGROUND

Many industrial processes are inherently hazardous. These processes typically use toxic, flammable, or reactive materials, and often at elevated temperatures and pressures. In the event of equipment malfunction or human error in these processes, a catastrophic event may occur. Safety instrumented systems (SIS) are automation systems designed to prevent these events. Interest, particularly in the chemical, petro-chemical, and refining industries, in these safety systems has increased recently due to international standards. In such safety instrumented systems, it is important to be able to diagnose malfunctions of the devices in the system.

In industrial processes where toxic gases are used, it is important that the detectors of such gases be constantly able to detect the presence of such gases. This is so even when the normal operating environment has virtually none of such toxic gases present. Moreover, such sensors and detection systems may be deployed in or around such hazardous industrial processes for a period of many years. When a release of toxic gas occurs, it is important that the sensor function effectively to quickly sense the toxic gas such that remedial action can be taken.

Electrochemical sensors are sometimes used within toxic gas detectors as the sensing element. With such sensors, the presence of a gas of interest causes an electrical change in the sensor that can be detected by suitable sensing circuitry. Examples of electrical characteristics include voltage, resistance, reactance, capacitance, or any other suitable electrical parameter.

SUMMARY

A detection system includes an electrochemical sensor. Measurement circuitry is coupled to the electrochemical sensor and configured to measure an electrical characteristic of the electrochemical sensor. A controller is coupled to the measurement circuitry and is configured to provide an indication based on the measured electrical characteristic. The controller is further configured to generate an electrical disturbance to the electrochemical sensor and obtain a sensor recovery profile to provide a diagnostic indication relative to the electrochemical sensor.

DETAILED DESCRIPTION OF ILLUSTRATIVE EMBODIMENTS

Figure 1:
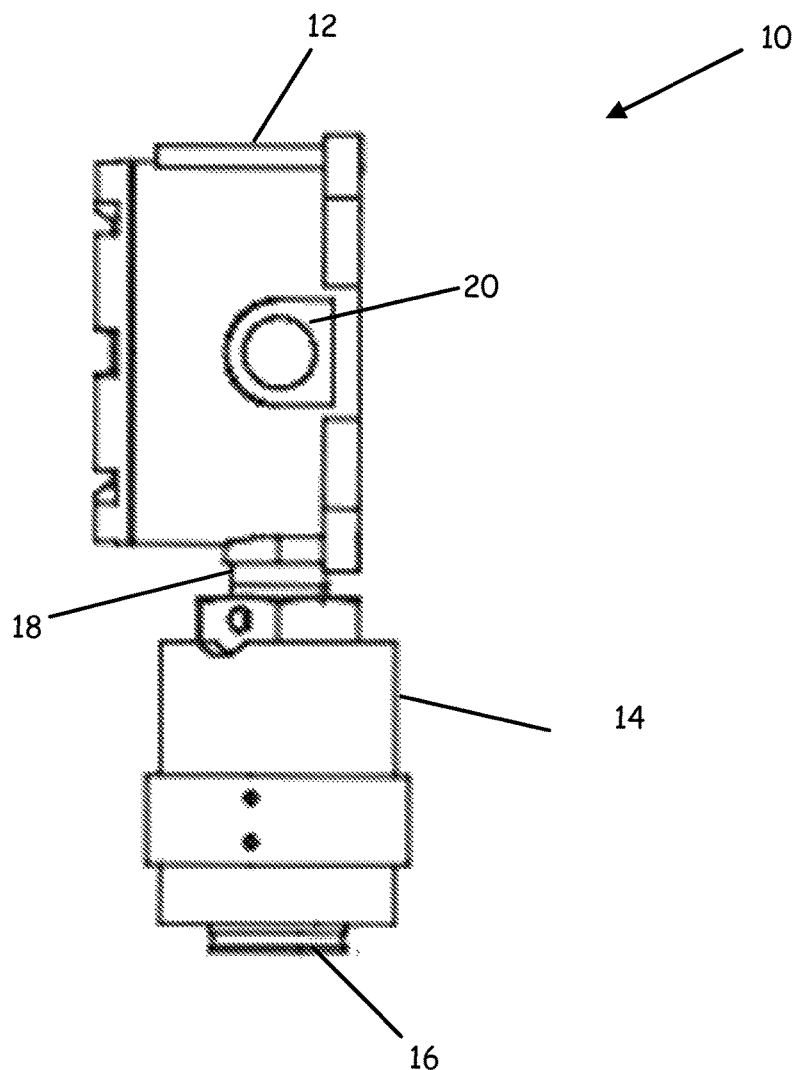
FIG. 1 is diagrammatic view of a gas detection system using an electrochemical gas detector cell in accordance with an embodiment of the present invention.

FIG. 1 is diagrammatic view of an electrochemical detection system using an electrochemical detector cell in accordance with an embodiment of the present invention. In one particular embodiment, the electrochemical detection system is a gas detection system. However, embodiments of the present invention are applicable to testing and electrochemical sensor.

System 10 includes electronics enclosure 12 coupled to sensor body 14. Sensor body 14 may include any suitable electrochemical sensor for which interaction with a gas of interest generates a detectable electrical response. Examples of such sensors include toxic gas sensors. Lower portion 16 of sensor body 14 is configured for exposure to ambient air in order to detect a gas of interest and potentially determine and provide a concentration indication relative to the gas of interest.

Toxic gasses that may be detected by the sensor include hydrogen sulfide, sulfur dioxide, carbon monoxide, chlorine, ammonia, and others. The sensor within sensor body 14 is coupled to suitable electronics (shown in FIG. 2) within enclosure 12 via conduit 18. Electronics within enclosure 12 can amplify, linearize, and otherwise characterize the sensor response in order to provide an indication of the gas concentration. This indication can be provided over a process communication loop or segment, via process wiring through conduit 20; provided locally via an alarm or display; and/or provided wirelessly via a suitable wireless process communication protocol, such as that specified in IEC62591. When a local indication of gas detection is provided, such indication may be in the form of a local operator interface indicating a display of gas presence and/or concentration, an audible or visual alarm, or any combination thereof.

Figure 2:
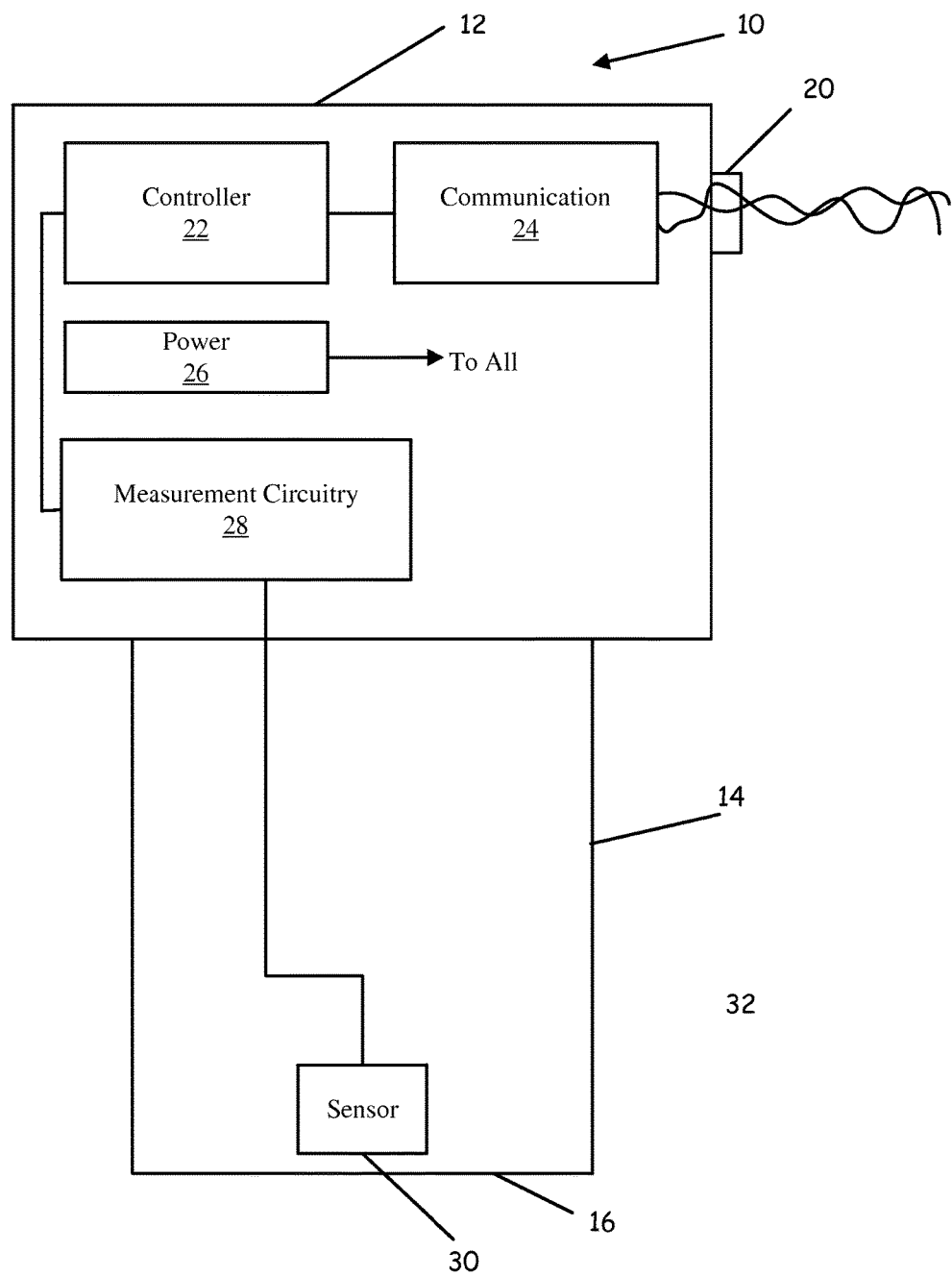
FIG. 2 is a block diagram of a gas detector in accordance with an embodiment of the present invention.

FIG. 2 is a diagrammatic view of a gas detection system in accordance with an embodiment of the present invention. System 10 includes electronics enclosure 12 coupled to sensor body 14. Disposed within electronics enclosure 12 are controller 22, communication module 24, power module 26, and measurement circuitry 28. Gas sensor 30 is disposed within sensor body 14 and is coupled to measurement circuitry 28.

Controller 22 may be any suitable processing circuitry that is able to interact with measurement circuitry 28 to obtain measurements relative to sensor 30 and provide an indication of gas presence and/or concentration based on the measurement. In one embodiment, controller 22 is able to execute a sequence of instructions to programmatically determine gas presence/concentration. In one embodiment, controller 22 is a microprocessor. Controller 22 is coupled to communication circuitry 24 to allow controller 22 to communicate with other devices in the process control and monitoring system. Communication circuitry 24 can include circuitry that allows controller 22 to communicate in accordance with process industry standard communication protocols, such as the Highway Addressable Remote Transducer (HART®) protocol, the FOUNDATION™ Fieldbus protocol, and others. In some embodiments, system 10 may communicate wirelessly in addition to or instead of using wired process communication. For example, in one embodiment, communication circuitry 24 may provide wireless process communication such as that set forth above in accordance with IEC62591. Finally, communication circuitry 24 may provide communication of local outputs, such as a local display, or alarm.

Power module 26 is coupled to all components within enclosure 12, as indicated by the arrow labeled "To All." Power module 26 is configured to receive power from a suitable source and provide voltage adjustment or other suitable power conditioning to the circuitry within enclosure 12. In some embodiments, power module 26 may be coupled to a wired process communication loop such that system 10 can receive all of its operating energy from the wired process communication loop. In other embodiments, power module 26 may be coupled to a suitable source of AC or DC power.

Measurement circuitry 28 is coupled to controller 22 and is able to obtain measurements from sensor 30 and provide digital indications thereof to controller 22. Measurement circuitry 28 may include an analog-to-digital converter, suitable multiplexor or switching circuitry, as well as amplification and/or linearization circuitry.

In accordance with an embodiment of the present invention, controller 22 is configured to engage measurement circuitry 28 or other suitable circuitry to momentarily generate an electrical disturbance to gas sensor 30 and subsequently monitor a recovery profile of sensor 30. In one embodiment, the disturbance is generated by shorting one conductor of sensor 30 to ground. Upon release of the short, measurement circuitry 28 will obtain a number of measurements from sensor 30 as the sensor signal transitions from the ground state to an indication of gas in the current ambient environment. The number of measurements that comprise the recovery profile is based on measurement circuitry 28 and the duration of the recovery. For example, if measurement circuitry 28 includes an analog-to-digital converter that is able to produce 50 measurements per second, sequentially obtaining and storing individual measurements over a period of two seconds will generate 100 samples. While the recovery period may be a fixed duration, it may also be based on the sensor signal achieving either steady-state, or some fixed percentage of its pre-disturbance value. Since the measurements are essentially obtained at a fixed frequency based on the circuitry of measurement circuitry 28, the storing of a number of measurement values by controller 22 creates a recovery profile of sensor 30. The recovery profile is useful in a couple of important regards. First, the total duration required for the sensor to recover may be indicative of proper functioning of the sensor. Second, the amplitude of the sensor signal as a function of time during the recovery can also be useful in determining whether the sensor is functioning properly. In one embodiment, the recovery profile is compared to a reference recovery profile either generated from the sensor when it was first commissioned or stored in controller 22 from the manufacturer of the device during manufacture. Further still, the reference recovery profile can be generated after system 10 is commissioned as long as a technician or operator indicates that the sensor is operating in a known-good condition.

Figure 3A:
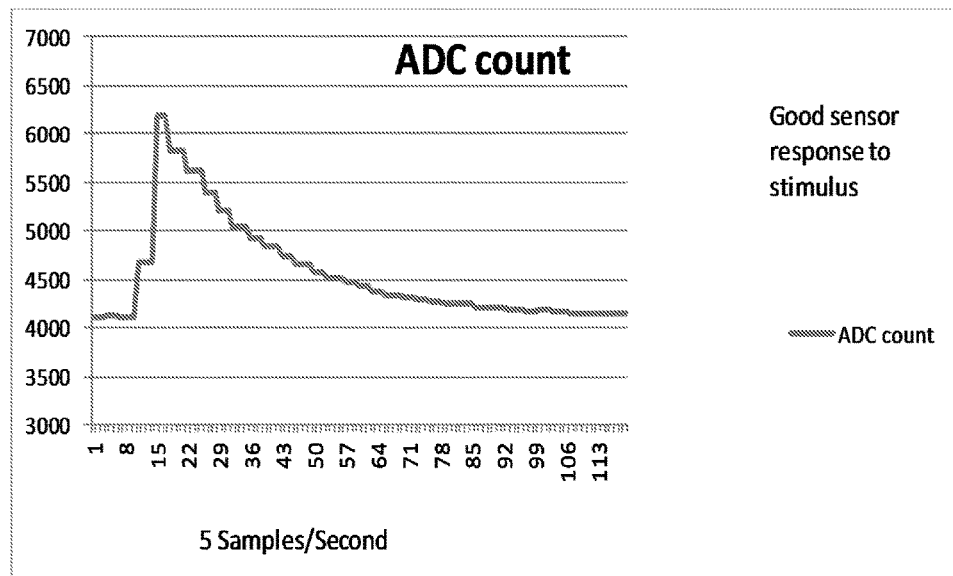
FIG. 3A is a diagrammatic view of gas sensor response versus time for a property-functioning sensor.

FIG. 3A is a diagrammatic view of gas sensor recovery profile for a properly-functioning sensor. As shown in FIG. 3A, the sensor output begins steady at approximately 4100 units, and at approximately count 15 is electrically disturbed, for example, by shorting one pin or conductor of the sensor to ground. When this short occurs, the sensor output quickly increases to approximately 6200 units. In the embodiment shown in FIG. 3A, the short is released virtually instantaneously and the sensor begins to recover. By count 90, the sensor has recovered and is back to indicating the gas concentration.

Figure 3B:
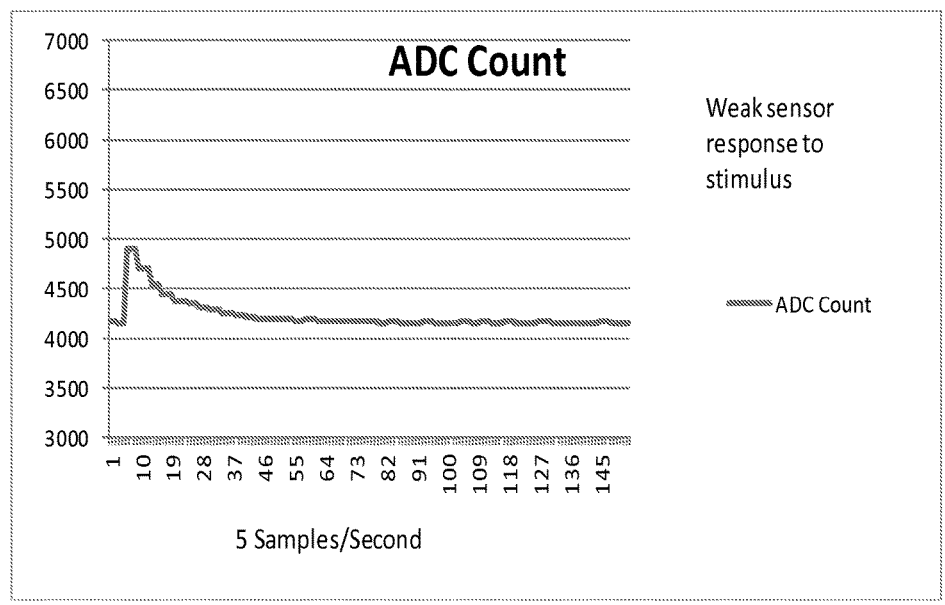
FIG. 3B is a diagrammatic view of a sensor recovery profile for a sensor that has degraded or has experienced a certain amount of wear.

In contrast, FIG. 3B shows a sensor recovery profile for a sensor that has degraded or has experienced a certain amount of wear. As in FIG. 3A, the sensor is initially reading a value of about 4100 units and is subject to an electrical disturbance at approximately count 7. The sensor output quickly increases, but not to the extent that it should. Instead the sensor response only increases to about 4900 units. Again, the electrical disturbance is released virtually instantaneously, and the sensor begins to recover. The sensor recovery is much quicker, and the sensor has substantially recovered from the disturbance by count 37. However, comparing FIG. 3B to FIG. 3A, the recovery period is substantially shorter, or at least substantially different, than the recovery period experienced for the nominal sensor (FIG. 3A). Additionally, the amplitude of the sensor signal as a function of time is significantly different than the profile illustrated in FIG. 3A. The difference in these recovery profiles can be used to calculate or otherwise extrapolate a period in the future when the sensor will no longer function properly. Accordingly, controller 22 can compare the sensor recovery profile with a reference recovery profile to generate an indication of remaining lifetime for the sensor. Further, based on the recovery signal profile, controller 22 is able to set a diagnostic status indication regarding whether the signal output from the electrochemical sensor or cell is valid or not. Further, such diagnostic indication can be indicative of a time in the future when the electrochemical cell output may not be valid.

Figure 4:
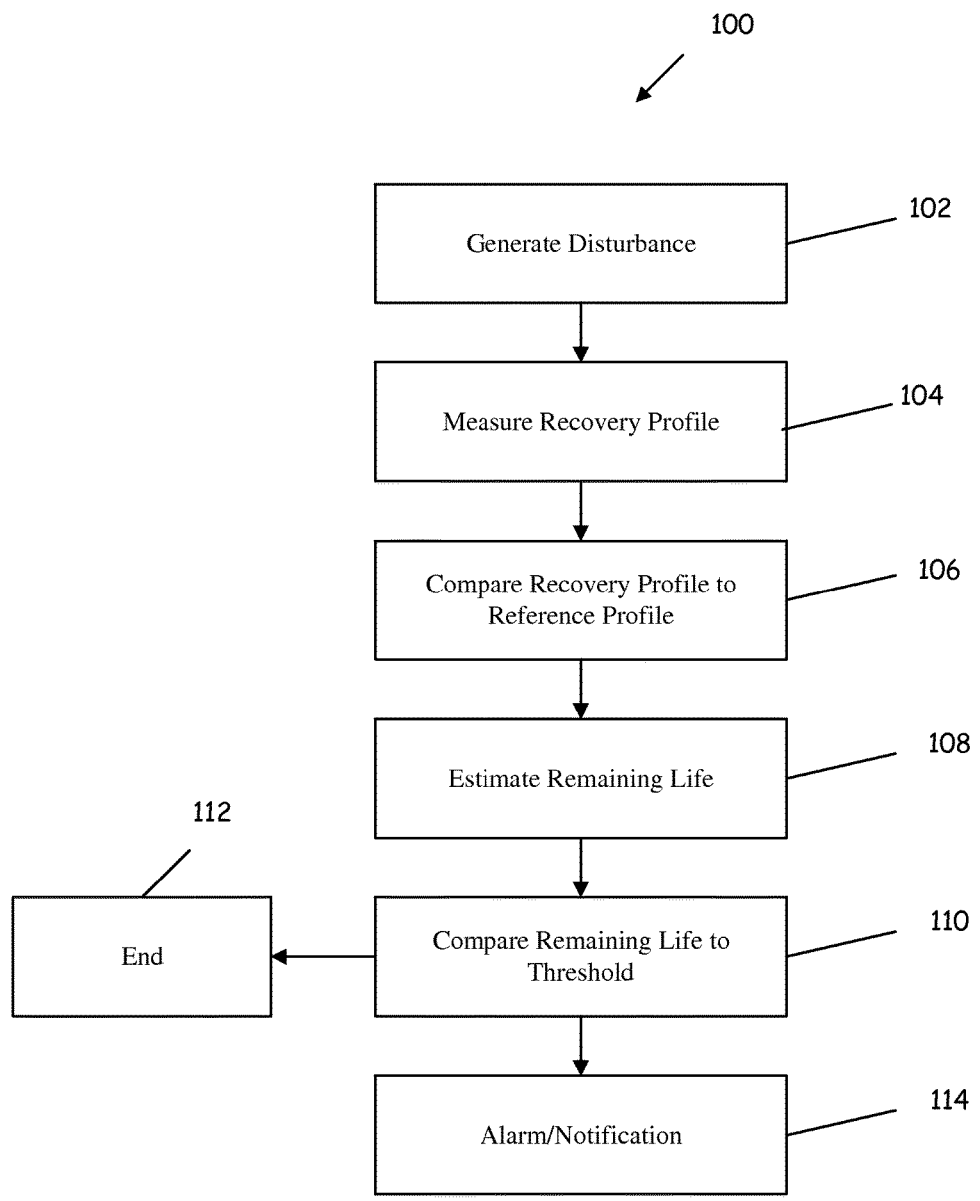
FIG. 4 is a flow diagram of a method of operating an electrochemical sensor in accordance with an embodiment of the present invention.

FIG. 4 is a flow diagram of a method of operating an electrochemical sensor in accordance with an embodiment of the present invention. Method 100 begins at block 102 where an electrical disturbance is generated to the electrochemical sensor. As set forth above, this electrical disturbance may be as simple as shorting one of the conductors of the electrochemical sensor to ground. However, other forms of electrical disturbances can be provided to the sensor. Next, at block 104, a sensor recovery profile is obtained as the sensor recovers from the disturbance generated in block 102. This sensor recovery profile is preferably stored in memory of controller 22 such that it can be analyzed once complete. At block 106, the sensor recovery profile is compared to reference recovery profile. This reference recovery profile may be provided by the manufacturer of the sensor or may be generated by the sensor itself when it is first commissioned. Further still, the reference recovery profile may be generated by a technician when a known-good condition exists for the sensor. At block 108, the comparison of the sensor recovery profile to the reference recovery profile is used to set a diagnostic status indication regarding whether the signal from the electrochemical sensor is valid or not. This indication may be that the sensor has reached its end of life, and is no longer valid. Alternatively, the indication may be a time in the future when the sensor output will no longer be valid or trustworthy. At block 110, the remaining life calculated at block 108 is compared to a threshold. For example, the threshold may be six months of remaining life, one year of remaining life, or any other suitable period. Based on this comparison, controller 22 may determine that the sensor lifetime is acceptable, and method 100 ends at block 112. Alternatively, if sufficient lifetime is not remaining, or if the sensor has no lifetime, control passes to block 114 where a suitable alarm or notification is generated. This alarm or notification may be provided locally and/or provided over a process communication loop or segment.

Although the present invention has been described with reference to preferred embodiments, workers skilled in the art will recognize that changes may be made in form and detail without departing from the spirit and scope of the invention.

What is claimed is:

1. A detection system comprising:
   an electrochemical sensor;
   measurement circuitry coupled to the electrochemical sensor and configured to measure an electrical characteristic of the electrochemical sensor;
   a controller coupled to the measurement circuitry, the controller being configured to provide an indication based on the measured electrical characteristic; and
   wherein the controller is further configured to send an electrical disturbance to the electrochemical sensor, generate a sensor recovery profile based on the measured electrical characteristic over a timeframe, and provide a diagnostic indication relative to the electrochemical sensor.

2. The detection system of claim 1, wherein the detection system is a gas detection system and wherein the electrochemical sensor is an electrochemical gas sensor where the electrical characteristic is responsive to at least one gas.

3. The detection system of claim 2, wherein the at least one gas includes a toxic gas.

4. The detection system of claim 1, wherein the measurement circuitry is configured to send the electrical disturbance based on a signal from the controller.

5. The detection system of claim 1, wherein the electrical disturbance includes coupling at least one conductor of the electrochemical gas sensor to ground.

6. The detection system of claim 1, wherein the diagnostic indication includes an indication of remaining life of the electrochemical sensor.

7. The detection system of claim 1, wherein the controller is configured to store the sensor recovery profile and compare the sensor recovery profile with a reference recovery profile in order to generate the diagnostic indication.

8. The detection system of claim 7, wherein the controller is configured to compare a duration of the sensor recovery profile with a duration of the reference recovery profile to generate the diagnostic indication.

9. The detection system of claim 7, wherein the controller is configured to compare amplitude of the sensor recovery signal as a function of time relative to the reference recovery profile to generate the diagnostic indication.

10. The detection system of claim 7, wherein the controller stores the reference recovery profile.

11. The detection system of claim 1, and further comprising process communication circuitry coupled to the controller, wherein the process communication circuitry is configured to communicate in accordance with a process communication protocol.

12. The detection system of claim 11, wherein the controller is configured to communicate the diagnostic indication over a process control loop using the process communication circuitry.

* * * * *